(12) United States Patent
Lenz et al.

(10) Patent No.: US 7,955,806 B2
(45) Date of Patent: Jun. 7, 2011

(54) DETECTION OF A THERAPEUTIC ANTIBODY IN AN EXPERIMENTAL ANIMAL

(75) Inventors: Helmut Lenz, Tutzing (DE);
Kay-Gunnar Stubenrauch, Penzberg (DE)

(73) Assignee: Hoffmann—La Roche Inc., Nutley, NJ (US)

( * ) Notice: Subject to any disclaimer, the term of this patent is extended or adjusted under 35 U.S.C. 154(b) by 590 days.

(21) Appl. No.: 11/792,910

(22) PCT Filed: Dec. 22, 2005

(86) PCT No.: PCT/EP2005/013849
§ 371 (c)(1),
(2), (4) Date: Jun. 12, 2007

(87) PCT Pub. No.: WO2006/066912
PCT Pub. Date: Jun. 29, 2006

(65) Prior Publication Data
US 2008/0102474 A1 May 1, 2008

(30) Foreign Application Priority Data

Dec. 23, 2004 (EP) ..................................... 04030545

(51) Int. Cl.
*G01N 33/53* (2006.01)
*G01N 33/564* (2006.01)
(52) U.S. Cl. ......................................... 435/7.1; 436/507
(58) Field of Classification Search ........................ None
See application file for complete search history.

(56) References Cited

U.S. PATENT DOCUMENTS 4,816,567 A    3/1989  Cabilly et al.
(Continued)

FOREIGN PATENT DOCUMENTS

EP          061888          10/1982
(Continued)

OTHER PUBLICATIONS

Stubenrauch et al. "Evaluation of an immunoassay for human-specific quantitation of therapeutic antibodies in serum samples from non-human primates" Journal of Pharmaceutical and Biomedical Analysis 49 (2009) 1003-1008.*

(Continued)

*Primary Examiner* — Gailene R Gabel
*Assistant Examiner* — Christine Foster
(74) *Attorney, Agent, or Firm* — George W. Johnston; Dennis P. Tramaloni

(57) ABSTRACT

The present invention relates to the field of therapeutic antibodies. It especially relates to the study of therapeutic antibodies in an experimental animal. The present invention discloses a method of detecting a therapeutic antibody in a sample obtained from an experimental animal comprising the steps of a) providing the sample to be analyzed, b) incubating said sample with an antibody binding to a therapeutic antibody and not binding to the immunoglobulin of said experimental animal, c) optionally incubating said sample with a reagent appropriate for the selective detection of total, active or antigen-bound therapeutic antibody, and d) correlating the complex formed in (b) or (c) to the concentration of said therapeutic antibody. A monoclonal antibody directed to a certain epitope that is present on all classes of human immunoglobulin of class G, but not on the immunoglobulin of any experimental animal except on the IgG of chimpanzees was used (MAB-M-R10Z8E9).

9 Claims, 9 Drawing Sheets

SA-MTP

MAB<IGF-1R>
MAB<H-Fcy>M-R10Z8E9-Bi    MAB<H-Fcy>M-R10Z8E9-DIG

PAB<DIG>-HRP

U.S. PATENT DOCUMENTS

| | | | | |
|---|---|---|---|---|
| 5,736,137 | A | * | 4/1998 | Anderson et al. ............ 424/133.1 |
| 5,821,337 | A | | 10/1998 | Carter et al. |
| 6,525,174 | B1 | * | 2/2003 | Young et al. .................. 530/350 |
| 7,008,796 | B2 | * | 3/2006 | Wohlstadter et al. ......... 436/172 |
| 2003/0068664 | A1 | | 4/2003 | Albitar et al. |
| 2004/0214761 | A1 | | 10/2004 | Raison et al. |

FOREIGN PATENT DOCUMENTS

| | | |
|---|---|---|
| EP | 1098198 | 5/2001 |
| JP | 2004191382 A | 11/2003 |
| WO | WO 9321319 | 10/1993 |
| WO | 98/04281 | 2/1998 |

OTHER PUBLICATIONS

Benincosa et al. "Pharmacokinetics and Pharmacodynamics of a Humanized Monoclonal Antibody to Factor IX in Cynomolgus Monkeys" J Pharmacol Exp Ther. Feb. 2000;292(2):810-6.*

Asada et al. "Molecular evolution of IgG subclass among nonhuman primates: Implication of differences in antigenic determinants among apes" Primates. Oct. 2002;43(4):343-9.*

Harlow, E. and Lane, D., Antibodies: A Laboratory Manual (1988) Cold Spring Harbor Laboratory Press, Cold Spring Harbor, NY, pp. 141-142.*

Carter, P. et al, Proc. Nat. Acad. Sci, 89 4285-4289 (1992).

Chothia, C et al, *J. Mol. Biiol*, 196 901-917 (1987).

Clackson, T. et al, *Nature*, 352 (1991) 624-28.

Hazelwood, M. et al, *Clin. Exp. Immunol*, 93:157-164 (1993).

Jones, P. et al, *Nature*, 321 522-525 (1986).

Kohler, G. et al, *Nature* 256: 495-497 (1975).

Lei, B. et al, *IVOS*, 41:1 262-266 (2000).

Marks, J. et al, *J. Mol. Biol.*, 222 581-597 (1991).

Nath, D. et al, *J. Biol Chem*. 270:44 26184-26191 (1995).

Presta, L. *Curr. Opin. in Structural Bio*, 2:593-596 (1992).

Presta L et al, *Jour. of Immun.*, 151:5 2623-2632 (1993).

Riechmann, L et al, *Nature*, 332: 323-327 (1988).

Sims, M. et al, *Jour. of Immun.*, 151:4 2296-2308 (1993).

Verhoeyen, M. et al, *Science*, 239, 1534-1536 (1988).

Tijssen, P. *Practice & Theory of Enzyme Immunassay*, 221-278 (1990).

Lü, X et al, *Jour. of Immun. Methods*, 197:193-196 (1996).

Hosoi S et al, Jour. of Allergy and Clinical Immunology, 75:2 (1985) 320-327 XP002592995.

Hamilton R G et al, Jour. of Immunological Methods, 158:1 (1993) 107-122 XP023992653.

European Search Report dated Aug. 25, 2010 issued in corresponding EP Appl. 10155679.3.

Hamilton, R.G. et al, Journal of Immunoassay 9 (1988) 275-296.

Dunstan, R.A. et al, Transfusion 24 (1984) 243-246.

Hungarian Patent Office Search dated Jan. 21, 2011 in Singapore Appl. 201005471-6.

\* cited by examiner

DETECTION OF A THERAPEUTIC ANTIBODY IN AN EXPERIMENTAL ANIMAL

The present invention relates to the field of therapeutic antibodies. It especially relates to the study of therapeutic antibodies in an experimental animal. The present invention discloses a method of detecting a therapeutic antibody in a sample obtained from an experimental animal comprising the steps of a) providing the sample to be analyzed, b) incubating said sample with an antibody binding to a therapeutic antibody and not binding to the immunoglobulin of said experimental animal, c) optionally incubating said sample with a reagent appropriate for the selective detection of total, active or antigen-bound therapeutic antibody, and d) correlating the complex formed in (b) or (c) to the concentration of said therapeutic antibody. It also relates to the use of an antibody which is binding to a therapeutic antibody and not binding to the immunoglobulin of an experimental animal for measuring the concentration of total, active, or antigen-bound therapeutic antibody in a sample obtained from an experimental animal.

Since the development of the first monoclonal antibodies by Koehler and Milstein in 1974 a lot of efforts have been dedicated to the development of antibodies which are appropriate for therapy in humans. The first monoclonal antibodies which became available had been developed in mice and rats. These antibodies when used for therapy of a human being caused unwanted side effects due to anti-rodent antibodies. A lot of efforts have been dedicated to the reduction or even elimination of such unwanted side effects.

In the past ten years an ever growing number of human monoclonal antibodies or humanized monoclonal antibodies have reached the market. Well-known examples include for example Herceptin® and MabThera® from Hoffmann-La Roche, Basel.

A quite significant number of human or humanized monoclonal antibodies is under investigation and needs to be studied in experimental animals, before entry into human can be considered for the first trial purposes.

Important criteria like bio-availability and antibody clearance just to mention two of them have to be studied by the aid of experimental animals. Many of these studies require the quantification of the therapeutic antibody in the background of the host's own antibodies. In most cases mammals are used as experimental animals. Toxicology often is first assessed in rodents like mice or rats. In the more advanced stages of drug development, especially before entry of the drug into human beings, even monkeys have to be included into such pre-clinical studies.

Mammals usually have between about 10 to about 30 milligram of immunoglobulin per ml in the circulation.

Therapeutic monoclonal antibodies typically have to be tested with serum levels ranging from about between 1 nanogram per ml to about 100 microgram per ml. The therapeutic antibody thus has to be detected against a background of host antibodies which is in an excess of about 100-fold to 10 million-fold. The detection of a human or humanized therapeutic antibody in the background of host immunoglobulin represents quite a significant task to the pharmacologist. In addition it will be appreciated that different therapeutic antibodies may require different reagents and assay formats. The detection of a human or humanized antibody becomes more and more difficult the closer the test animal is related to *H. sapiens*.

It was a task of the present invention to investigate whether methods of detecting a therapeutic antibody in a sample obtained from an experimental animal can be improved. It was also investigated whether a human or a humanized therapeutic antibody can be studied in sera of monkeys, especially in sera of lesser apes. This task has been accomplished by the invention as described below and in the examples section and as claimed in the appending claims.

In a first embodiment the present invention relates to a method of detecting a therapeutic antibody in a sample obtained from an experimental animal comprising the steps of a) providing the sample to be analyzed, b) incubating said sample with an antibody binding to a therapeutic antibody and not binding to the immunoglobulin of said experimental animal, c) optionally incubating said sample with a reagent appropriate for the selective detection of total, active or antigen-bound therapeutic antibody, and d) correlating the complex formed in (b) or (c) to the concentration of said therapeutic antibody.

The term "therapeutic antibody" relates to any antibody preparation which is intended for use in a human being. Preferably such therapeutic antibody will be a monoclonal antibody. Further preferred such monoclonal antibody will be obtained from a great ape or be a human monoclonal antibody. Preferably, it will be a human monoclonal antibody. Also preferred such therapeutic monoclonal antibody will be a humanized monoclonal antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Koehler, G., et al., Nature 256 (1975) 495-497, or may be made by recombinant DNA methods (see, e.g., U.S. Pat. No. 4,816,567). The "monoclonal antibodies" may also be isolated from phage antibody libraries using the techniques described in Clackson, T., et al., Nature 352 (1991) 624-628 and Marks, J. D., et al., J. Mol. Biol. 222 (1991) 581-597, for example.

"Humanized" forms of non-human (e.g., rodent) antibodies are chimaeric antibodies that contain partial sequences derived from non-human immunoglobulin and from a human immunoglobulin. For the most part, humanized antibodies are derived from a human immunoglobulin (recipient antibody) in which residues from a hypervariable region of the recipient are replaced by residues from a hypervariable region of a non-human species (donor antibody) such as mouse, rat, rabbit or non-human primate having the desired specificity and affinity. In some instances, framework region (FR) residues of the human immunoglobulin are replaced by corresponding non-human residues. Furthermore, humanized antibodies may comprise further modifications, e.g., amino acid residues that are not found in the recipient antibody or in the donor antibody. Such modifications result in variants of such recipient or donor antibody which are homologous but not identical to the corresponding parent sequence. These modifications are made to further refine antibody performance. In general, the humanized antibody will comprise substantially all of at least one, and typically two, variable domains, in which all or substantially all of the hypervariable loops correspond to those of a non-human donor antibody and all or substantially all of the FRs are those of a human recipient antibody. The humanized antibody optionally also will comprise at least a portion of an immunoglobulin constant region (Fc), typically that of a human immunoglobulin.

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones, P. T., et al., Nature 321 (1986) 522-525; Riechmann, L., et al., Nature, 332 (1988) 323-327; Verhoeyen, M., et al., Science, 239 (1988) 1534-1536 and Presta, L. G., Curr. Op. Struct. Biol., 2 (1992) 593-596), by substituting hypervariable region sequences for the corresponding sequences of a non-human antibody. Accordingly, such "humanized" antibodies are chimaeric antibodies (U.S. Pat. No. 4,816,567), wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims, M. J., et al., J. Immunol., 151 (1993) 2296-2308; Chothia, C., et al., J. Mol. Biol. 196 (1987) 901-917). Another method uses a particular framework region derived from the consensus sequence of all human antibodies of a particular subgroup of light or heavy chains. The same framework may be used for several different humanized antibodies (Carter, P., et al., Proc. Natl. Acad. Sci. USA, 89 (1992) 4285-4289; Presta, L. G., et al., J. Immunol. 151 (1993) 2623-2632).

Well known examples of humanized therapeutic antibodies are the so-called anti-ErbB2 antibodies including huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as described in Table 3 of U.S. Pat. No. 5,821,337 expressly incorporated herein by reference; as well as humanized 520C9 (described in WO 93/21319) and humanized 2C4 antibodies as described in PCT/US 03/21590.

The term "variant" refers to polypeptides having amino acid sequences that differ to some extent from a native polypeptide sequence. Ordinarily, a variant amino acid sequence variant will possess at least about 80% homology with the corresponding parent antibody sequence, and preferably, they will be at least about 90%, more preferably at least about 95% homologous with such corresponding parent antibody sequence. The amino acid sequence variants possess substitutions, deletions, and/or insertions at certain positions within the amino acid sequence of the native amino acid sequence.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

The term "experimental animal" as used herein denotes the members of the families of the order of primates comprising marmosets and tamarins (family Callitrichidae), new world monkeys (family Cebidae), old world monkeys (family Cercopithecidae), dwarf and mouse lemurs (family Cheirogaleidae), aye-aye (family Daubentoniidae), bushbabies and galagos (family Galagonidae), gibbons and lesser apes (family Hylobatidae), indris, sifakas, and relatives (family Indridae), true lemurs (family Lemuridae), lorises (family Loridae), sportive lemurs (family Megaladapidae), tarsiers (family Tarsiidae), as well as crossings thereof.

Preferably the method according to the present invention will be practiced in experimental animals selected from the group comprising the members of the families of marmosets and tamarins, old world monkeys, dwarf and mouse lemurs, gibbons and lesser apes, true lemurs, as well as crossings thereof. In this preferred embodiment the closest relatives to mankind, the great apes, especially the group of chimpanzees, bonobos, gorillas and orangutans is excluded.

A "sample" according to the present invention may be any tissue or liquid sample removed from the experimental animal. Preferably the sample will be a liquid sample like Saliva, urine, whole blood, plasma or serum. Preferably the sample will be whole blood, plasma or serum.

An "antibody binding to a therapeutic antibody and not binding to the immunoglobulin of an experimental animal" will bind to a therapeutic antibody with a dissociation constant (=KDiss.) of at least $10^{-9}$ mol/L, more preferred with a KDiss. of at least $10^{-10}$ mol/L. At the same time the property of not binding to the immunoglobulin of the experimental animal is insured by a KDiss. of $10^{-8}$ mol/L or worse. Also preferred, the antibody binding to a therapeutic antibody and not binding to the immunoglobulin of an experimental animal will have a KDiss.-gap of at least 100-fold between its reactivity towards the IgG of an experimental animal and towards human IgG, respectively.

The binding properties of an antibody, especially the KDiss., preferably is assessed by a Biacore® instrument. In this method binding properties are evaluated by changes in surface plasmon resonance (SPR). It is convenient to bind the antibody under investigation to the solid phase (called chip) and to assess binding of a monoclonal antibody, a polyclonal antibody or even of serum comprising IgG to this coated chip.

The antibody binding to a therapeutic antibody and not binding to the immunoglobulin of the experimental animal under investigation may be a polyclonal antibody, a monoclonal antibody, fragments of such antibodies, as well as genetic constructs comprising the binding domain of such antibody. Any antibody fragment retaining the above criteria of binding to the therapeutic antibody and of non-binding to the immunoglobulin of said experimental animal can be used. Antibodies as well as antibody fragments are generated by state of the art procedures, e.g., as described in Tijssen (Tijssen, P., Practice and theory of enzyme immunoassays 11 (1990), the whole book, especially pages 43-78, Elsevier, Amsterdam).

As indicated further above, various aspects connected to the application of a therapeutic antibody in an experimental animal may have to be assessed during pre-clinical studies. In certain settings it may be relevant to analyze the total amount of therapeutic antibody present, or it may be important to analyze certain fragments of a therapeutic antibody, certain modifications of a therapeutic antibody, the concentration of therapeutic antibody bound to an antigen or the fraction of therapeutic antibody still capable of binding to an antigen. Preferably the method according to the present invention is used to detect the total, active, or antigen-bound therapeutic antibody, respectively.

The term "total" therapeutic antibody refers to any antibody detected irrespective of whether the antibody is active (i.e., still reactive with its antigen), inactive, and/or antigen-bound.

The term "active" therapeutic antibody relates to the therapeutic antibody present in an experimental animal that still is capable of binding its antigen. Such antibodies, e.g., have not bound its antigen or any other molecule at its antigen binding site.

The term "antigen-bound" therapeutic antibody is used to indicate the therapeutic antibody as present in the circulation of an experimental animal that is bound to its antigen.

Total, active or antigen-bound therapeutic antibody as defined above can be directly detected in a method according to the present invention.

In addition, it is also possible to indirectly assess any "inactive" therapeutic antibody. Such inactive therapeutic antibody may, e.g., be a therapeutic antibody bound to its antigen, the therapeutic antibody bound to a cross-reactive antigen, or the therapeutic antibody blocked by an auto antibody against the therapeutic antibody. As the skilled artisan will appreciate, it is possible by aid of the present disclosure to assess the fraction of inactive antibody. In case the total antibody amounts to more than the sum of active antibody and antigen-bound antibody, an additional fraction of antibody comprising the inactive antibody not bound to its corresponding antigen will be present.

Various assay systems are at hand to analyze e.g., total, active or antigen-bound therapeutic antibody.

Total antibody for example can be detected in a so-called competitive immunoassay system or in a so-called sandwich type assay system.

Such assay may be performed without washing steps (homogeneous immunoassay) or with washing steps (heterogeneous immunoassay).

Preferably total therapeutic antibody is detected in a sandwich type immunoassay, wherein the antibody which is binding to a therapeutic antibody and not binding to the immunoglobulin of the experimental animal is used at both sides of such sandwich assay. The antibody used at one side of such sandwich is bound or capable of binding to a solid phase (often referred to as capture antibody), whereas the antibody at the other side of such sandwich is labeled in such a manner that direct or indirect detection is facilitated (so-called detection antibody). The amount of detection antibody bound in such sandwich assay procedure is directly correlated to the amount of therapeutic antibody in the sample investigated.

In the art (e.g. US 2003/0068664) assay systems are known, which allow for the detection of active therapeutic antibodies. Such systems require the binding of the antigen to a solid phase, binding of the therapeutic antibody to this bound antigen and detection of the therapeutic antibody bound via the antigen to the solid phase.

Detection of active therapeutic antibody in a sample may be achieved by convenient state of the art procedures. However, the detection of total therapeutic antibody or of the fraction of therapeutic antibody bound to its antigen is rather complicated and requires quite different assay set-ups and especially requires tailor-made reagents for each of the different assays. With the antibody according to the present invention that is binding to a therapeutic antibody and not binding to the immunoglobulin of the experimental animal it is possible to assess the fraction of active therapeutic antibody, total therapeutic antibody, or antigen-bound therapeutic antibody in test systems which are analogues to each other. By its very nature this kind of comparative assessment of total, active, or antigen-bound therapeutic antibody should have big advantages once quantitative comparisons are made in between these various fractions of therapeutic antibody.

Preferably a sandwich type assay format is (also) set up to detect the active therapeutic antibody. Preferably, the antibody which is binding to a therapeutic antibody and not binding to the immunoglobulin of the experimental animal is used as a capture antibody and the detection side of such sandwich assay either makes use of the antigen in a labeled form or after binding of the antigen makes use of a second antibody not binding to or competing with the epitope recognized by the therapeutic antibody, wherein said second antibody is specifically detectable and/or is labeled in such a manner that direct or indirect detection is facilitated.

The antigen-bound therapeutic antibody preferably is detected in a sandwich type assay format again preferably using the antibody binding to a therapeutic antibody and not binding to the immunoglobulin of the experimental animal as a capture reagent. In the detection preferably a second antibody is used binding to the antigen at an epitope which does not compete with the epitope of the therapeutic antibody. Said second antibody preferably is labeled in such a manner that direct or indirect detection is facilitated.

For direct detection the labeling group can be selected from any known detectable marker groups, such as dyes, luminescent labeling groups such as chemiluminescent groups, e.g. acridinium esters or dioxetanes, or fluorescent dyes, e.g. fluorescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay, e.g. EP-A-0 061 888), and radioisotopes.

Indirect detection systems comprise, for example, that the detection reagent, e.g., the detection antibody is labeled with a first partner of a bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g., steroid hormone receptor/steroid hormone. Preferred first binding pair members comprise hapten, antigen and hormone. Especially preferred are haptens like digoxin and biotin and analogues thereof. The second partner of such binding pair, e.g. an antibody, streptavidin, etc., usually is labeled to allow for direct detection, e.g., by the labels as mentioned above.

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates (in: "Practice and theory of enzyme immunoassays" (1990), pp. 221-278, Eds. R. H. Burdon and v. P. H. Knippenberg, Elsevier, Amsterdam) and various volumes of "Methods in Enzymology" (Eds. S. P. Colowick, N. O. Caplan, Academic Press), dealing with immunological detection methods, especially volumes 70, 73, 74, 84, 92 and 121.

In all the above immunological detection methods reagent conditions are chosen which allow for binding of the reagents employed, e.g. for binding of an antibody to its corresponding antigen. The skilled artisan refers to the result of such binding event by using the term complex. The complex formed in an assay method according to the present invention is correlated by state of the art procedures to the corresponding concentration of said therapeutic antibody. Depending on the detection reagent employed this correlating step will result in the concentration of total, active or antigen-bound therapeutic antibody.

As the skilled artisan will appreciate the methods according to the present invention will not only reveal the concentrations of total, antigen-bound, active or even inactive therapeutic antibody. Due to the preferred use of one and the same reagent, the antibody binding to a therapeutic antibody and not binding to the immunoglobulin of said experimental animal, in the different assays the values obtained can be easily compared to each other and even ratios thereof assessed. In a further preferred embodiment the present invention relates to the ratio of active to total therapeutic antibody. This ratio may well serve as an indicator for the efficacy of a therapeutic antibody.

During the course of the experiments leading to the present invention it has been found that a certain epitope that is present on all classes of human immunoglobulin of class G appears not to be present on the immunoglobulin of any experimental animal except on the IgG of chimpanzees. This epitope is characterized by its binding to MAB<H-Fcγ pan>M-R10Z8E9, also denoted MAB<h-Fc gamma>M-R10Z8E9, or briefly MAB M-R10Z8E9. In a preferred embodiment according to the present invention the antibody binding to a therapeutic antibody and not binding to the immunoglobulin of an experimental animal is further characterized in that said antibody is an antibody binding to the same epitope as MAB M-R10Z8E9. MAB M-R10Z8E9 has been deposited with DSMZ on Dec. 22, 2004 as DSM ACC2708.

Preferably the present invention relates to a monoclonal antibody that binds to a therapeutic antibody that monoclonal antibody having an antigen combining site which competitively inhibits the binding of monoclonal antibody MAB M-R10Z8E9 as produced by this hybridoma deposited with the DSMZ. The term "competitively inhibits" means being able to recognize and bind the epitope as recognized by monoclonal antibody M-R10Z8E9. Such binding is easily assessed using conventional reciprocal antibody competition assays.

In brief, in a reciprocal competition experiment it is investigated whether two (or more) specific binding agents inhibit the binding of one another to the same antigen or epitope. If say antibodies A and B are investigated for binding to the same epitope. Both these antibodies will compete for binding if they bind to the same epitope. Binding to the same epitope is present if antibody A at equimolar concentration reduces binding of B by at least by 20% and vice versa.

As the skilled artisan appreciates competition may be assessed in different assay set-ups.

Preferably the Biacore® system, see above, is used. Binding of an antibody under investigation to the same epitope as bound by MAB M-R10Z8E9 is present if the antibody under investigation at equimolar concentration reduces the binding of MAB M-R10Z8E9 to human IgG by 20% or more and if MAB M-R10Z8E9 reduces the binding of said antibody to human IgG by 20% or more.

In yet a further preferred embodiment MAB M-R10Z8E9 is used as the antibody binding to a therapeutic antibody and not binding to the immunoglobulin of the experimental animal in a method according to the present invention.

As mentioned above, the therapeutic antibody detected in a method according the present invention preferably is human or a humanized monoclonal antibody. Preferably the therapeutic antibody used in a method according to the present invention comprises the epitope as bound by MAB M-R10Z8E9.

In a further preferred embodiment the present invention relates to the use of an antibody which is binding to a therapeutic antibody and not binding to the immunoglobulin of an experimental animal for measuring the concentration of total, active, or antigen-bound therapeutic antibody in a sample obtained from an experimental animal. Preferably the antibody used in such method is an antibody binding to the epitope as recognized by MAB M-R10Z8E9.

The following examples, references, and figures are provided to aid the understanding of the present invention, the true scope of which is set forth in the appended claims. It is understood that modifications can be made in the procedures set forth without departing from the spirit of the invention.

The biotinylated monoclonal antibody (MAB<H-Fcγ pan>-M-R10Z8E9-Bi) is bound to a streptavidin-coated microtiter plate (SA-MTP). The therapeutic antibody MAB<IGF-1R> is bound and indirectly detected via digoxigenin-labeled MAB<H-Fcγ pan>M-R10Z8E9-DIG and an anti-digoxigenin horse-radish peroxidase conjugate (PAB<DIG>HRP).

Figure 1:
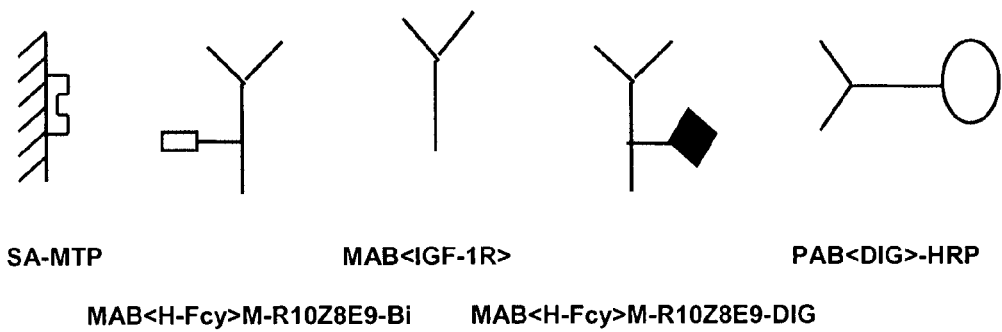
FIG. 1 Detection of total therapeutic antibody
Figure 2:
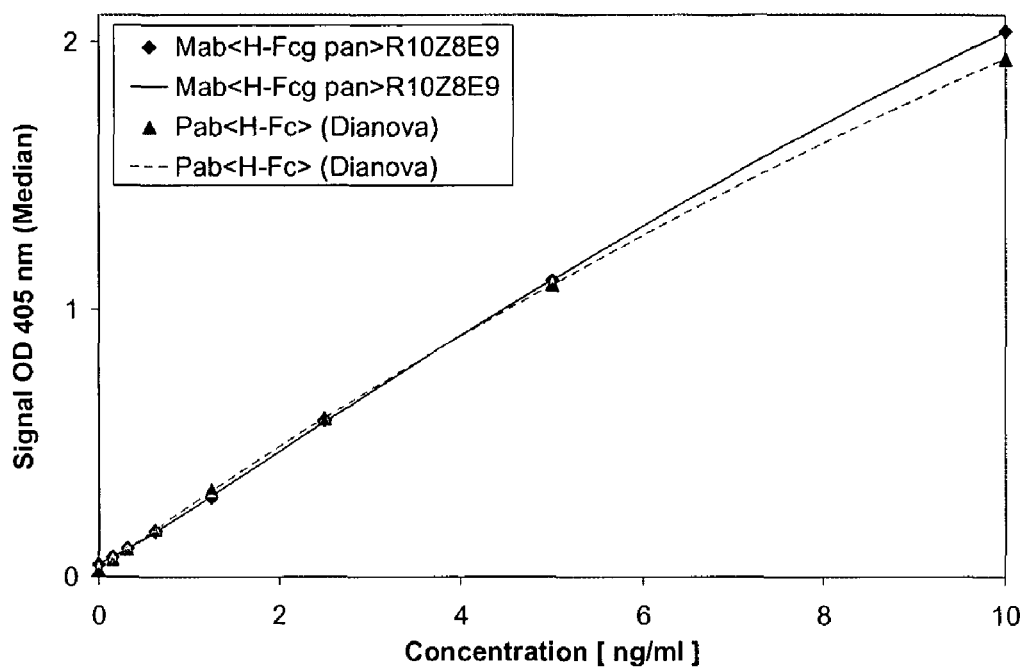

FIG. 2: Detection of total therapeutic antibody diluted in buffer

The optical densities (ODs) are given for the various concentrations of therapeutic antibody as diluted in PBS-T, 0.5% BSA (w/v).

Figure 3:
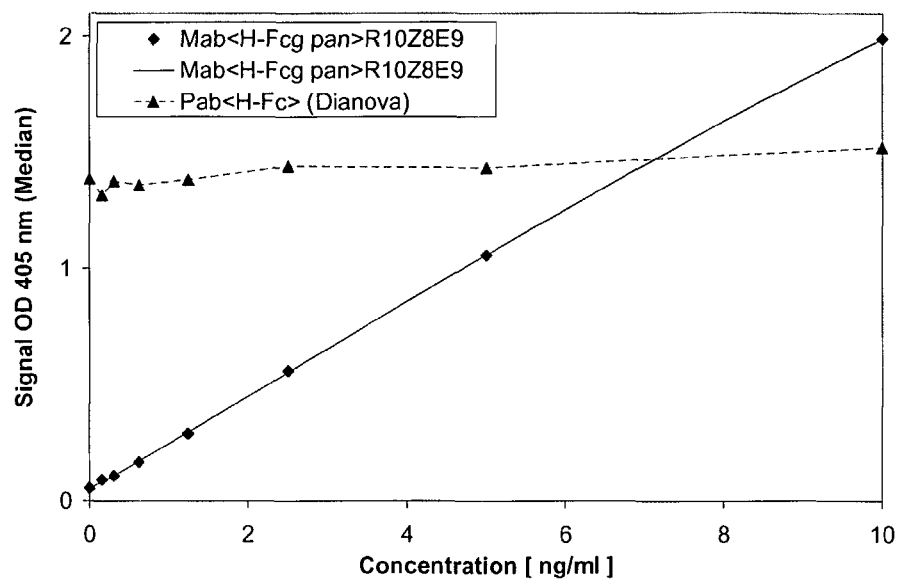

FIG. 3: Detection of total therapeutic diluted in buffer but also containing 5% (v/v) cynomolgus serum The optical densities (ODs) are given for the various concentration of therapeutic antibody as diluted in PBS-T, 0.5% BSA with 5% (v/v) cynomolgus serum.

Figure 4:
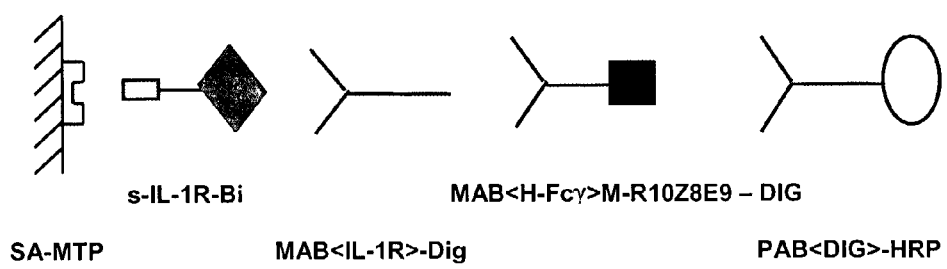

FIG. 4: Detection of active therapeutic antibody via solid-phase antigen

This cartoon shows the reagents used in the detection of active therapeutic antibody via a solid-phase bound antigen. In the specific example given biotinylated soluble interleukin 1 receptor (s-IL-1R-Bi) is bound to the wells of a streptavidin-coated microtiter plate (SA-MTP). Active therapeutic antibody binds to the antigen and is indirectly detected via digoxigenylated anti-human antibody (MAB<H-Fcγ pan>M-R10Z8E9-DIG) and anti-DIG-HRP (PAB<DIG>HRP).

Figure 5:
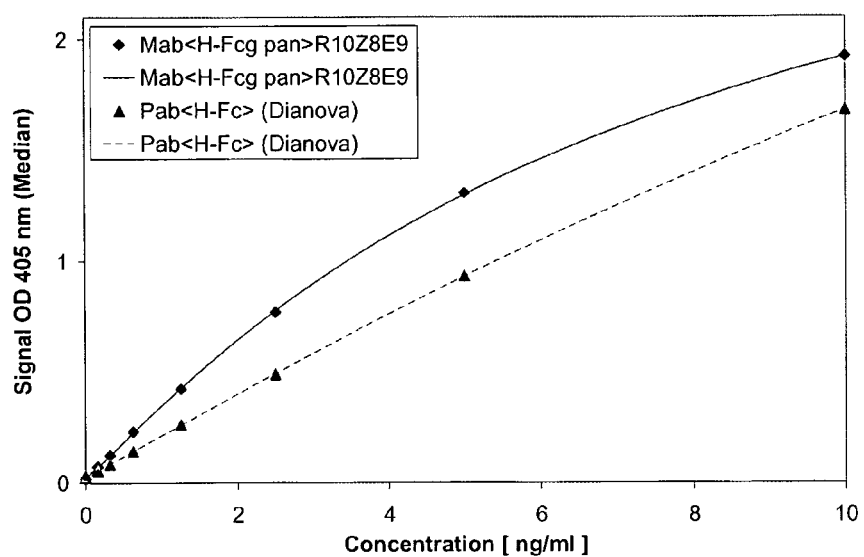

FIG. 5: Detection of active therapeutic antibody diluted in buffer

The optical densities (ODs) are given for the various concentrations of therapeutic antibody as diluted in PBS-T, 0.5% BSA.

Figure 6:
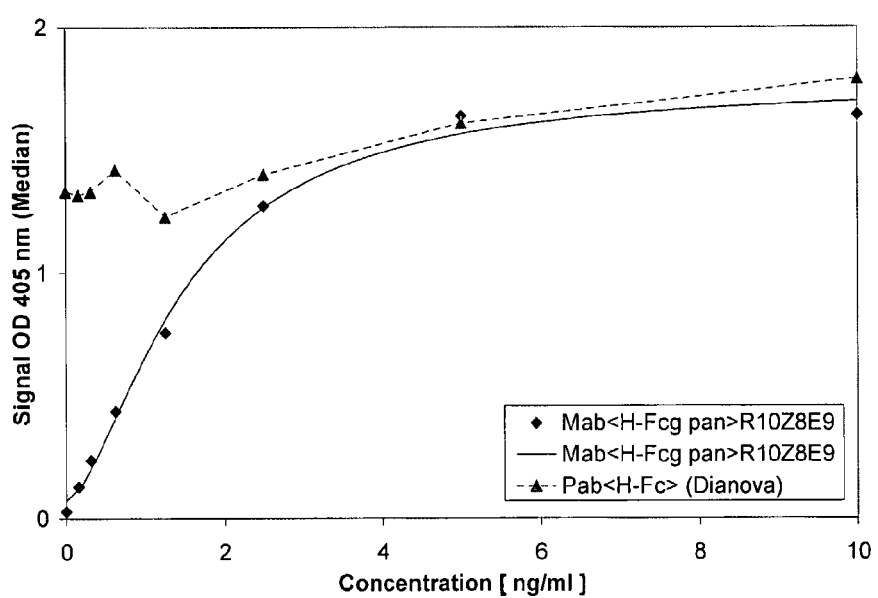

FIG. 6: Detection of active therapeutic antibody diluted in buffer additionally comprising 5% cynomolgus serum The optical densities (ODs) are given for the various concentration of therapeutic antibody as diluted in PBS-T, 0.5% BSA with 5% cynomolgus serum.

Figure 7:
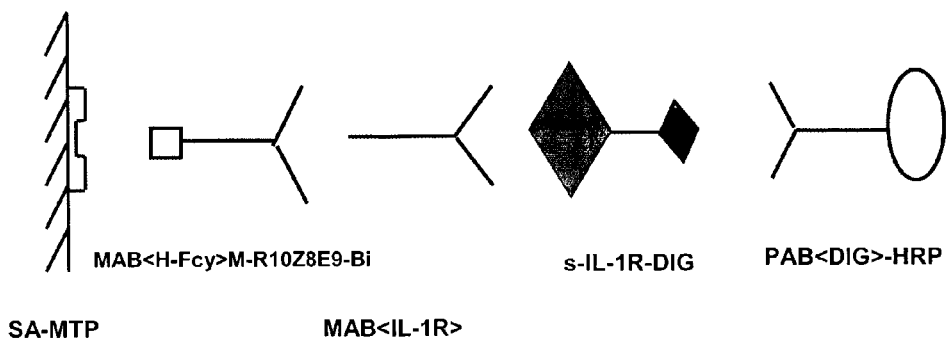

FIG. 7: Detection of active therapeutic antibody in a sandwich assay format

The biotinylated monoclonal antibody (MAB<H-Fcγ pan>-M-R10Z8E9-Bi) is bound to a streptavidin-coated microtiter plate (SA-MTP). Detection is indirect employing the digoxigenin-labeled antigen (s-IL-1R-DIG) and an anti-digoxigenin horse-radish peroxidase conjugate (PAB<DIG>HRP).

Figure 8:
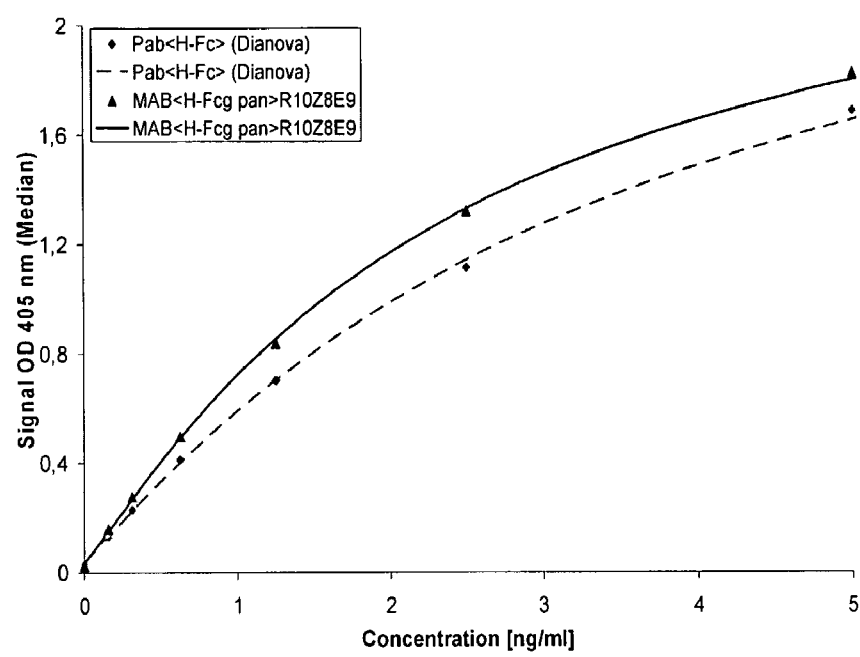

FIG. 8: Detection of active therapeutic antibody diluted in buffer via a sandwich assay The optical densities (ODs) are given for the various concentrations of therapeutic antibody as diluted in PBS-T, 0.5% BSA.

Figure 9:
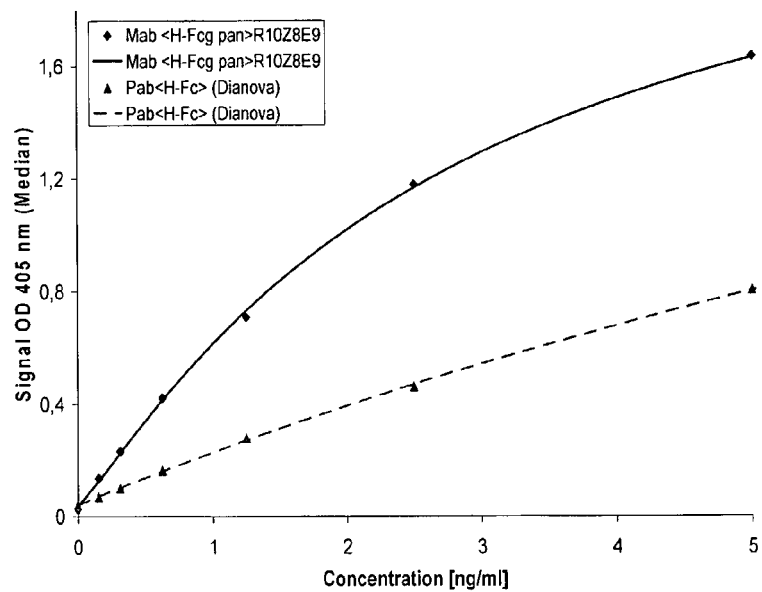

FIG. 9: Detection of active therapeutic antibody diluted in buffer additionally comprising 5% cynomolgus serum via a sandwich assay The optical densities (ODs) are given for the various concentration of therapeutic antibody as diluted in PBS-T, 0.5% BSA with 5% cynomolgus serum.

ABBREVIATIONS

ABTS 2,2'-Azino-di-[3-ethylbenzthiazoline sulfonate (6)] diammonium salt
BSA bovine serum albumin
ELISA enzyme-linked immunosorbent assay
Fcγ =Fcγ=Fcg=Fcgamma=Fc gamma-fragment of an immunoglobulin
POD (=HRP) horse-radish peroxidase
IgG immunoglobulin G
DIG (Dig) digoxigenin
MTP microtiter plate
OD optical density
PBS phosphate buffered saline
SDS sodium dodecyl sulfate
MAK (=Mab) monoclonal antibody
PAK (=Pab) polyclonal antibody
RT room temperature
SA streptavidin
T Tween®20
<human IgG> antibody against human IgG

Example 1

Assessment of Specificity a) Use of Various Anti-Human IgG Antibodies in an MTP-ELISA A microtiter plate (MTP) (Maxisorb®, Nunc) was coated with monkey (e.g. cynomolgus) and with human serum diluted to 20% in carbonate buffer (pH 9.6), at room temperature (RT) for 1 hour, respectively. After washing 3 times with PBS-Tween®20, all wells of the MTPs were blocked with PBS/3% BSA at room temperature for 1 hour. Then the wells of the MTPs were incubated (1 h; RT) with different anti-human IgG antibodies (un-conjugated, or anti-human IgG antibody horseradish peroxidase (POD) conjugates (see Table 1)). The various anti-human antibodies were used as recommended by the corresponding manufacturer.

Wells were washed three times as above. Wells incubated with POD-conjugates were directly processed for enzymatic reaction/detection of bound anti-human immunoglobulin. The other wells were incubated (1 h; RT) as appropriate with anti-Dig-, anti-mouse IgG- or streptavidin-POD-conjugates (all reagents from Roche Diagnostics, Germany) followed by a washing step. The POD comprised in the POD-conjugates catalyzes the color reaction of ABTS substrate. The signal was measured by an ELISA reader at a wavelength of 405 nm (reference wavelength: 490 nm). For every anti-human IgG antibody the ratio of the signal against human antibodies to the signal of cynomolgus sera was calculated. These values were used for evaluation of the specificity of the anti-human IgG antibodies. A high ratio translates to a strong reactivity with human immunoglobulin and at the same time to a low (cross-) reactivity with monkey immunoglobulin.

TABLE 1

Reactivity of anti-human antibodies with human and cynomolgus monkey serum

| Antibody | Signal in 10% (v/v) HumanSerum | Signal in 10% (v/v) cynomolgus serum | Signal Ratio Human/Cynom. |
|---|---|---|---|
| MAK<Human IgG> MK1A6 // Chemicon # CBL101 (*) | 0.743 | 0.895 | 0.83 |
| PAK<Human IgG>-Bi // Dako # E0428 (**) | 2.066 | 1.815 | 1.14 |
| MAK<H-Fcγ pan> M-R10Z8E9-Dig (***) | 1.847 | 0.032 | 58.63 |
| MAK<H-Fcγ pan> M-R10Z8E9 (*) | 1.779 | 0.199 | 8.96 |
| MAK<Human Agg-IgG>IgM-Dig (***) | 1.541 | 0.700 | 2.20 |
| MAK<Human Kappa>R12Z6H9-Dig (***) | 1.566 | 0.720 | 2.17 |
| MAK<Hu-IgG> F(ab')2-HRP // Dianova # 109-066-098 | 1.401 | 0.953 | 1.47 |
| MAK<Human IgG> HRP // Chemicon # AP 113P | 0.973 | 0.574 | 1.70 |
| PAK<Human IgG>F(ab)'2-HRP // Dako # P0406 | 0.513 | 0.431 | 1.19 |
| MAK<Human IgG>-HRP // Boehringer Mannheim (alt) | 1.383 | 0.796 | 1.74 |
| Controls: | | | |
| <Mouse>-HRP | 0.139 | 0.131 | 1.07 |
| <Dig>-HRP | 0.029 | 0.031 | 0.94 |
| SA-HRP | 0.193 | 0.288 | 0.67 |

(*) = Detection with <Mouse>-HRP
(**) = Detection with SA-HRP
(***) = Detection with <Dig>-HRP The high signal ratio for human serum as compared to cynomolgus serum observed for MAB<H-Fcγ pan>M-R10Z8E9 indicates the high human-specificity of MAB<H-Fcγ pan>M-R10Z8E9. In contrast to MAB<H-Fcγ pan>M-R10Z8E9 all other tested antibodies show a high cross-reactivity.

Based on the above encouraging data the cross-reactivity of MAB<H-Fcγ pan>M-R10Z8E9 against other immunoglobulin from other relevant experimental animals was investigated.

Wells of a microtiter plate were coated with serum from various experimental animals. The assay was performed as described above, using the MAB<H-Fcγ pan>M-R10Z8E9 as specific anti-human IgG detection reagent.

As can be seen from Table 2 MAB<H-Fcγ pan>M-R10Z8E9 exclusively reacts with the immunoglobulin of human serum human IgG or chimpanzee serum respectively.

Reactivity of MAB<H-Fcγ pan>M-R10Z8E9 with mouse, rat, dog, monkey and human serum, is shown in Tables 2a and b, respectively TABLE 2a Detection with MAB<H-Fcγ pan>M-R10Z8E9-Dig // <Dig>-POD

| Serum (10% (v/v)) | Signal | Signal Ratio Human/Animal |
|---|---|---|
| Dog | 0.096 | 19.24 |
| Rat | 0.034 | 54.32 |
| CD1-Mouse | 0.028 | 65.96 |
| NMRI-Mouse | 0.065 | 28.42 |
| Cynomolgus | 0.032 | 58.63 |
| Baboon | 0.029 | 63.69 |
| Rhesus macaque | 0.031 | 60.56 |
| Marmoset | 0.128 | 14.43 |
| Chimpanzee | 1.865 | 0.99 |
| Human | 1.847 | 1.00 |
| Human IgG (5 µg/ml) | 1.821 | 1.01 |

TABLE 2b

Detection with anti-mouse IgG POD conjugates

| Serum (10% (v/v)) | Signal | Signal Ratio Human/Animal |
|---|---|---|
| Cynomolgus | 0.199 | 8.96 |
| Baboon | 0.131 | 13.63 |
| Rhesus macaque | 0.186 | 9.59 |
| Marmoset | 0.239 | 7.46 |
| Chimpanzee | 1.893 | 0.94 |
| Human | 1.779 | 1.00 |
| Human IgG (5 µg/ml) | 2.105 | 0.85 |

It is interesting to note that in the above indirect detection systems the quality of the final reagent <DIG>-POD or <mouse>-POD used in indirect detection also influences the signal to noise ratio. The skilled artisan will choose a detection reagent with little or no binding to the IgG of an experimental animal.

b) Assessing Antibody Binding/Specificity by the Biacore® System

All measurements were performed with the Biacore® 2000 instrument using a CM5-chip. Coating of an antibody to this chip was achieved by standard amine coupling. Unless otherwise indicated all incubations were performed in HBS-buffer (HEPES, NaCl, pH 7.4) at 25° C.

A saturating amount of MAB<H-Fcγ pan>M-R10Z8E9 and polyclonal anti-human Fcγ antibody (Dianova), respectively, was immobilized by amine coupling on different channels of the same CM5-chip. All animal sera were diluted in HBS buffer containing 1 mg/ml CM-dextran at a final concentration of 1%. Binding was analyzed by injection of the 1 in 100 diluted sera and incubation for 60 seconds. Dissociation was measured by washing the chip surface with HBS buffer for 180 seconds. Using Biaevaluation Software from Biacore® the dissociation constant values (=KDiss.) were calculated with a 1:1 Langmuir fitting model. For all animal sera this calculation was based on the assumption that the IgG level is 15 mg/ml. The signal values 80 seconds after start of the injection of the test antibody have been chosen for the comparison of the amount of IgG bound (RU in table 2c and 2d).

TABLE 2c

Binding signals [RU] of animal sera to MAB<H-Fcγ pan>M-R10Z8E9 and a polyclonal anti-human-Fcγ antiserum

| Sample | MAB<H-Fcγ pan>M-R10Z8E9 | | PAB<H-Fcγ>(Dianova) | |
|---|---|---|---|---|
| (Serum) | Bound RU | KD in M | Bound RU | KD in M |
| Human | 2377 | $1.83 \times 10^{-10}$ | 2399 | $5.64 \times 10^{-11}$ |
| Cynomolgus | 8 | no binding | 1929 | $6.24 \times 10^{-11}$ |
| CD1-Mouse | 2 | no binding | 0 | no binding |
| NMRI Mouse | 5 | no binding | 3 | no binding |
| Rat | 25 | no binding | 92 | $5.28 \times 10^{-8}$ |
| Dog | 634 | $8.12 \times 10^{-8}$ | 925 | $6.21 \times 10^{-10}$ |

TABLE 2d

Binding signals [RU] of different monkey sera to MAB<H-Fcγ pan>M-R10Z8E9 and a polyclonal anti-human-Fcγ antiserum

| Sample (Serum) | MAB<H-Fcγ pan>M-R10Z8E9 | | PAB<H-Fcγ>(Dianova) | |
|---|---|---|---|---|
| | Bound RU | KDiss. in M | Bound RU | KDiss. in M |
| Human | 1274.0 | $1.77 \times 10^{-10}$ | 1854.2 | $2.81 \times 10^{-11}$ |
| Cynomolgus 1 | 2.9 | no binding | 1591.9 | $6.64 \times 10^{-11}$ |
| Cynomolgus 2 | 2.8 | no binding | 1413.1 | $5.21 \times 10^{-11}$ |
| Cynomolgus 3 | 6.3 | no binding | 1899.0 | $1.15 \times 10^{-10}$ |
| Baboon | 0 | no binding | 1209.8 | $7.33 \times 10^{-11}$ |
| Marmoset | 5.1 | no binding | 433.9 | $1.02 \times 10^{-9}$ |
| Chimpanzee | 1077.5 | $2.21 \times 10^{-10}$ | 1967.5 | $1.21 \times 10^{-12}$ |
| Rhesus Macaque | −2.9 | no binding | 1409.9 | $4.86 \times 10^{-11}$ |

The SPR-analysis (of the different monkey sera) confirms the results seen in the MTP ELISA. MAB<H-Fcγ pan>M-R10Z8E9 does not cross-react with any monkey species. Only the IgG comprised in human and chimpanzee (greater ape) serum is detected. In contrast to the MTP ELISA some binding of dog serum to MAB<H-Fcγ pan>M-R10Z8E9. The relatively high KDiss. for dog IgG (correlating to inferior binding) as compared to human IgG with a KDiss.-gap of more than 100-fold indicates, that this low interaction does not interfere significantly in an immunoassay. This is actually what has been found in the MTP ELISA of Example 1a).

In contrast to MAB<H-Fcγ pan>M-R10Z8E9 the polyclonal anti-human Fc antibody shows a high cross-reactivity with sera of dog and all tested monkey species.

Example 2

Use of MAB<H-Fcγ pan>M-R10Z8E9 for Quantification of Total Therapeutic Antibody

Biotinylated MAB<H-Fcγ pan>M-R10Z8E9 or polyclonal antibody directed against human Fc was bound to streptavidin-coated microtiter plates (SA-MTP) in the first step. The excess of unbound antibody was removed by washing. Samples/standards, e.g. MAB <IGF-1R> spiked in cynomolgus serum, were simultaneously pre-incubated with digoxigenylated MAB<H-Fcγ pan>M-R10Z8E9-DIG) for 1 hour. Afterwards the mixture was added to wells of an SA-MTP coated with the biotinylated <human IgG> antibodies and incubated for 1 hour. After washing the bound digoxingenylated MAB<H-Fcγ pan>M-R10Z8E9 was detected with an anti-digoxigenin-antibody. The POD of the antibody-enzyme conjugates catalyzes the color reaction of ABTS substrate. The signal is measured by Elisa reader at 405 nm wavelength (reference wavelength: 490 nm). Absorbance values of each serum sample were determined in triplicates.

TABLE 3

Comparison of standard curve in buffer (PBS-T, 0.5% BSA)

| concentration of MAB<IGF-1R> [ng/ml] | signal OD 405 nm | |
|---|---|---|
| | MAB<H-Fcγ pan>M-R10Z8E9 | PAB<H-Fcγ> (Dianova) |
| 10 | 2.039 | 1.937 |
| 5 | 1.109 | 1.094 |
| 2.5 | 0.586 | 0.593 |
| 1.25 | 0.296 | 0.326 |
| 0.625 | 0.170 | 0.176 |
| 0.313 | 0.108 | 0.106 |
| 0.156 | 0.075 | 0.068 |
| 0 | 0.046 | 0.027 |

As can be seen from Table 3 and FIG. 2 both anti-Human Fc-gamma antibodies are suitable for quantification of human antibodies (MAB <IGF-1R>), if spiked into buffer. However, in the presence of monkey IgG's (5% cynomolgus serum) the performance of the ELISA with the polyclonal AB<H-Fcγ> became significantly worse. (Table 4 and FIG. 3)

TABLE 4

Comparison of standard curves in 5% cynomolgus serum

| concentration of MAB<IL-1R> [ng/ml] | signal OD 405 nm | |
|---|---|---|
| | MAB<H-Fcγ pan>M-R10Z8E9 | PAB<H-Fcγ> (Dianova) |
| 10 | 1.990 | 1.5230 |
| 5 | 1.057 | 1.4335 |
| 2.5 | 0.559 | 1.4410 |
| 1.25 | 0.289 | 1.3840 |
| 0.625 | 0.166 | 1.3610 |
| 0.313 | 0.108 | 1.3780 |
| 0.156 | 0.091 | 1.3170 |
| 0 | 0.054 | 1.3870 |

Caused by cross-reactivity of PAB<H-Fcγ> (Dianova) with monkey IgG a true or correct quantification of human IgG in monkey serum is not possible.

Example 3

Use of MAB<H-Fcγ pan>M-R10Z8E9 in Quantification of Active Human Antibody MAB<IL-1R>

Biotinylated soluble human IL-1 receptor (h-IL-1R-Bi) was bound to streptavidin-coated microtiter plates (SA-MTP) in the first step. The excess of unbound receptor was removed by washing. Afterwards MAB<IL-1R> spiked in cynomolgus serum was bound to the immobilized human IL-1 receptor. After washing away unbound substances the bound MAB<IL-1R> was detected with a) digoxigenylated monoclonal antibody against human IgG chains (MAB<H-Fcγ pan>M-R10Z8E9-DIG) followed by incubation with a horse-radish peroxidase labeled anti-Digoxigenin-antibody; or with b) polyclonal anti-human Fc antibodies (Dianova) followed by a wash step. The POD comprised in the antibody-enzyme conjugates catalyzes the color reaction of ABTS substrate. The signal is measured by ELISA reader at 405 nm wavelength (reference wavelength: 490 nm). Absorbance values of each serum sample are determined in triplicates.

TABLE 5

Detection of total therapeutic antibody

| concentration of MAB<IL-1R> [ng/ml] | signal OD 405 nm | |
|---|---|---|
| | MAB<H-Fcγ pan>M-R10Z8E9 | PAB<H-Fcγ> (Dianova) |
| 10 | 1.921 | 1.682 |
| 5 | 1.307 | 0.933 |
| 2.5 | 0.770 | 0.489 |
| 1.25 | 0.424 | 0.262 |
| 0.625 | 0.231 | 0.143 |
| 0.313 | 0.125 | 0.084 |
| 0.156 | 0.074 | 0.057 |
| 0 | 0.020 | 0.031 |

TABLE 6

Detection of total therapeutic antibody in cynomolgus Serum

| concentration of MAB<IL-1R> [ng/ml] | signal OD 405 nm | |
|---|---|---|
| | MAB<H-Fcγ pan>M-R10Z8E9 | PAB<H-Fcγ> (Dianova) |
| 10 | 1.642 | 1.789 |
| 5 | 1.637 | 1.608 |
| 2.5 | 1.272 | 1.400 |
| 1.25 | 0.755 | 1.228 |
| 0.625 | 0.435 | 1.419 |
| 0.313 | 0.236 | 1.331 |
| 0.156 | 0.128 | 1.315 |
| 0 | 0.027 | 1.332 |

The data given in Tables 5 and 6 and shown in FIGS. 5 and 6 demonstrate that both anti-human Fc-gamma antibodies are suitable for quantification of active human antibodies (MAB<IL-1R>) spiked into buffer. However in the presence of monkey IgG (5% (v/v) cynomolgus serum) the performance of the ELISA with the polyclonal AB<H-Fcγ> became significantly worse. Caused by cross-reactivity with monkey IgG the sensitivity decreased and the variability increased.

Example 4

Use of MAB<H-Fcγ pan>M-R10Z8E9 in Quantification of Active MAB<IL-1R> in Monkey Serum Biotinylated MAB<H-Fcγ pan>M-R10Z8E9 or biotinylated polyclonal anti-human IgG directed against human Fc (b) was bound onto the wells of a streptavidin-coated microtiter plates (SA-MTP) in the first step. The excess of unbound antibody was removed by washing. Afterwards the MAB<IL-1R> spiked into cynomolgus serum was bound to the immobilized anti-human antibody. After washing away unbound substances the bound MAB<IL-1R> was detected with digoxigenylated soluble human IL-1 receptor (h-IL-1R-Dig) followed by incubation with a horse-radish peroxidase labeled anti-digoxigenin-antibody. The antibody-enzyme conjugate catalyzes the color reaction of ABTS substrate. The signal is measured by ELISA reader at 405 nm wavelength (reference wavelength: 490 nm). Absorbance values of each serum sample are determined in triplicates.

A cartoon exemplifying this test system is shown as FIG. 7.

TABLE 7

Comparison of the standard curves in buffer (PBS-T, 0.5% BSA)

| concentration of MAB<IL-1R> [ng/ml] | signal OD 405 nm | |
|---|---|---|
| | MAB<H-Fcγ pan>M-R10Z8E9 | PAB<H-Fcγ> (Dianova) |
| 5 | 1.824 | 1.685 |
| 2.5 | 1.319 | 1.112 |
| 1.25 | 0.837 | 0.702 |
| 0.625 | 0.497 | 0.413 |
| 0.313 | 0.277 | 0.229 |
| 0.156 | 0.159 | 0.132 |
| 0 | 0.025 | 0.032 |

TABLE 8

Comparison of the standard curves in 5% cynomolgus serum

| concentration of MAB<IL-1R> [ng/ml] | signal OD 405 nm | |
|---|---|---|
| | MAB<H-Fcγ pan>M-R10Z8E9 | PAB<H-Fcγ> (Dianova) |
| 5 | 1.635 | 0.805 |
| 2.5 | 1.179 | 0.460 |
| 1.25 | 0.707 | 0.278 |
| 0.625 | 0.421 | 0.163 |
| 0.313 | 0.231 | 0.101 |
| 0.156 | 0.136 | 0.070 |
| 0 | 0.026 | 0.04 |

If the therapeutic antibody is diluted in PBS-T with 5% BSA both anti-human antibodies work (cf. Table 7 and FIG. 8). However, in the presence of monkey IgG (5% cynomolgus serum) the performance of the ELISA using the polyclonal AB<H-Fcγ> is poor. The signal out-put is much lower despite the same amount of therapeutic antibody present, as shown in Table 8 and FIG. 9. Caused by cross-reactivity with monkey IgG the assay performance depends on the total amount and composition of monkey IgG, which can vary from animal to animal and from time-point to time-point.

LIST OF REFERENCES

Carter, P., et al., Proc. Natl. Acad. Sci. USA, 89 (1992) 4285-4289
Chothia, C., et al., J. Mol. Biol. 196 (1987) 901-917
Clackson, T., et al., Nature 352 (1991) 624-628
Colowick, S. P., Caplan, N. O. (eds.), Methods in Enzymology, Academic Press Computer program "Align 2" by Genentech, Inc., United States Copyright Office, Washington, D.C. 20559, Dec. 10, 1991
EP-A 0 061 888
Jones, P. T., et al., Nature 321 (1986) 522-525
Koehler, G., et al., Nature 256 (1975) 495-497
Marks, J. D., et al., J. Mol. Biol. 222 (1991)581-597
Presta, L. G., et al., J. Immunol. 151 (1993) 2623-2632
Presta, L. G., Curr. Op. Struct. Biol. 2 (1992) 593-596
Riechmann, L., et al., Nature 332 (1988) 323-327
Sims, M. J., et al., J. Immunol. 151 (1993) 2296-2308
Tijssen, P., "Practice and theory of enzyme immunoassays", R. H. Burdon and v. P. H. Knippenberg (eds.), Elsevier, Amsterdam, 1990, pp. 221-278; especially pp. 43-78
US 2003/0068664
U.S. Pat. No. 5,821,337
U.S. Pat. No. 4,816,567
Verhoeyen, M., et al., Science 239 (1988) 1534-1536
WO 93/21319

The invention claimed is:

1. A method of detecting a therapeutic antibody in a sample obtained from an experimental animal comprising the steps of
    a) providing the sample to be analyzed,
    b) incubating said sample with a monoclonal antibody binding to said therapeutic antibody and not binding to the immunoglobulin of said experimental animal, wherein the monoclonal antibody is an antibody binding to the same epitope as MAB M-R10Z8E9, deposited as ACC 2708,
    c) optionally incubating said resulting sample of (b) with a reagent appropriate for the selective detection of total, active or antigen-bound therapeutic antibody, and
    d) correlating the complex formed in (b) or (c) to the concentration of said therapeutic antibody.

2. The method according to claim 1, wherein said experimental animal is selected from the group consisting of the members of the families of marmosets and tamarins, old world monkeys, dwarf and mouse lemurs, gibbons and lesser apes, true lemurs, and crossings thereof.

3. The method of claim 1, wherein said therapeutic antibody is a human or a humanized antibody.

4. The method of claim 3, wherein said human or humanized antibody is a monoclonal antibody.

5. The method of claim 1, wherein total therapeutic antibody is detected.

6. The method of claim 1, wherein active therapeutic antibody is detected.

7. The method of claim 1, wherein therapeutic antibody is detected which is bound to its antigen.

8. A method for measuring the concentration of total, active, or antigen-bound therapeutic antibody in a sample obtained from an experimental animal, wherein said method comprises
    a) obtaining a sample from an experimental animal, wherein said sample contains immunoglobulin of said animal,
    b) incubating said sample with a monoclonal antibody binding to said therapeutic antibody and not binding to the immunoglobulin of said experimental animal, wherein the monoclonal antibody is an antibody binding to the same epitope as MAB M-R10Z8E9, deposited as ACC 2708,
    c) optionally incubating said resulting sample of (b) with a reagent appropriate for the selective detection of total, active or antigen-bound therapeutic antibody, and
    d) correlating the complex formed in (b) or (c) to the concentration of said therapeutic antibody.

9. A homogeneous method of detecting a therapeutic antibody in a sample obtained from an experimental animal comprising the steps of
    a) providing the sample to be analyzed,
    b) incubating said sample with a monoclonal antibody binding to said therapeutic antibody and not binding to the immunoglobulin of said experimental animal, wherein the monoclonal antibody is an antibody binding to the same epitope as MAB M-R10Z8E9, deposited as ACC 2708, c) optionally incubating said resulting sample of (b) with a reagent appropriate for the selective detection of total, active or antigen-bound therapeutic antibody, and d) correlating the complex formed in (b) or (c) to the concentration of said therapeutic antibody, wherein said homogeneous method does not require washing between steps a)-b) or steps a)-c).

* * * * *